United States Patent [19]

Aumueller et al.

[11] Patent Number: 4,835,273
[45] Date of Patent: May 30, 1989

[54] GLYCOLURIL DERIVATIVES

[75] Inventors: Alexander Aumueller, Deidesheim; Peter Neumann, Wiesloch; Hubert Trauth, Dudenhofen, all of Fed. Rep. of Germany

[73] Assignee: BASF Aktiengesellschaft, Ludwigshafen, Fed. Rep. of Germany

[21] Appl. No.: 133,625

[22] Filed: Dec. 16, 1987

[30] Foreign Application Priority Data

Dec. 22, 1986 [DE] Fed. Rep. of Germany ....... 3643892

[51] Int. Cl.$^4$ ................. C07D 251/72; C07D 401/14; C07D 487/22; C07D 401/06
[52] U.S. Cl. ................................. 544/180; 544/216; 544/215
[58] Field of Search ........................ 544/180, 216, 215

[56] References Cited

U.S. PATENT DOCUMENTS 4,769,457  9/1988  Helwig et al. ..................... 544/180

FOREIGN PATENT DOCUMENTS 213570  3/1987  European Pat. Off. .
2291203  6/1976  France .

*Primary Examiner*—John M. Ford
*Attorney, Agent, or Firm*—Oblon, Fisher, Spivak, McClelland & Maier

[57] ABSTRACT

Compounds useful for stabilizing organic material have the general formula (I)

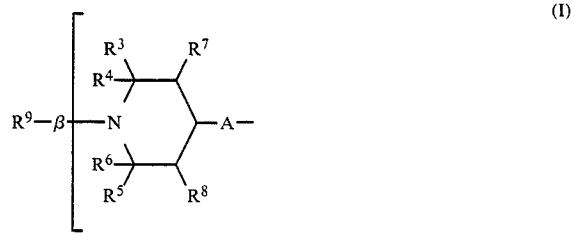

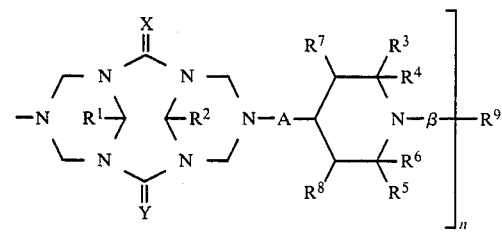

where the substituents are as defined in claim 1.

19 Claims, No Drawings

GLYCOLURIL DERIVATIVES

It is known that 2,2,6,6-tetraalkylpiperidine derivatives are light stabilizers for organic polymers. FR-A-2,291,203 describes glycoluril derivatives of the formula where R is optionally substituted hydrocarbyl of up to 22 carbon atoms. These compounds are proposed for use as surfactants for the textile industry and as corrosion inhibitors.

Earlier EP-A-213,570 describes glycoluril derivatives having 2,2,6,6-tetraalkylpiperidine substituents as light stabilizers for organic materials. In these compounds, the tetraalkylpiperidine radical is in each case bonded directly to the heterocyclic ring system.

Unsatisfactory aspects are frequently the compatibility of these agents in particular with polyolefins, the duration of the stabilizing action, the volatility and self-color of the substances.

It is an object of the present invention to provide new glycoluril derivatives which are suitable for stabilizing organic material and which are free of the abovementioned disadvantages.

We have found that this object is achieved with the compounds of the general formula (I)

where:
n is a number from 1 to 70,
$R^1$ and $R^2$ are independently of each other hydrogen, $C_1$–$C_6$-alkyl, $C_7$–$C_{12}$-aralkyl, aryl or carboxylate, or $R^1$ and $R^2$ together form a tetra-, penta- or hexamethylene group or an optionally substituted radical of the formula $R^3$, $R^4$, $R^5$ and $R^6$ are independently of each other alkyl,
$R^7$ and $R^8$ are independently of each other hydrogen or alkyl or together with the associated carbon atom form a $$\diagdown C=O$$

group,
X and Y independently of each other have the meanings oxygen, sulfur or $NR^{10}$, where $R^{10}$ is hydrogen, $C_1$–$C_8$-alkyl, $C_7$–$C_{12}$-aralkyl,
$R^9$ is hydrogen, $C_1$–$C_{22}$-alkyl which may be substituted by hydroxyl, carbonyl, carboxylate, carboxyl, carbamoyl, sulfonyl, sulfinyl or thiol, $C_3$–$C_{22}$-alkenyl, $C_3$–$C_{22}$-alkynyl, $C_7$–$C_{12}$-aralkyl, $C_1$–$C_{22}$-alkyl, $C_4$–$C_{22}$-cycloalkyl-alkyl, an optionally substituted heterocyclic, chlorine, bromine, iodine, hydroxyl, alkoxy, carboxyl, carboxylate, sulfonamido, optionally substituted carbamoyl, a urea group, a urethane group or —(CH$_2$T$_k$D where k is a number from 1 to 10 and D is —CN, —NH$_2$—, —NHR$^{11}$ or —NR$^{11}$R$^{12}$, where $R^{11}$ and $R^{12}$ are identical or different and each is $C_1$–$C_{22}$-alkyl, C-acyl, carbamoyl, sulfonyl, sulfinyl, $C_2$–$C_{22}$-alkenyl, $C_3$–$C_{22}$-alkynyl, $C_3$–$C_{12}$cycloalkyl, aralkyl or oligomeric or polymeric polyamine, which radicals may be further substituted, or where $R^{11}$ and $R^{12}$ together with the nitrogen atom to which they are bonded form a 3- to 20-membered ring system, the
A's are identical or different and each is a direct bond or a bridge member, with the proviso that one or more of the radicals A is a bridge member if $R^9$ does not have the meaning —(CH$_2$)$_k$—D, and
B is a further bridge member or a direct bond,
and the acid addition salts and hydrates thereof.

The present invention also describes the use of compounds of the general formula I and mixtures thereof for stabilizing organic material, in particular plastics and paints.

Preference is given to the use of compounds according to the invention for stabilizing polyolefins, polyamides and paints.

A particularly preferred use is for light and heat stabilization and as a metal ion deactivator, in particular in plastics.

Specific examples of $R^1$ and $R^2$, besides hydrogen, are methyl, ethyl, propyl, butyl, pentyl, hexyl, benzyl, phenylethyl, phenylpropyl, phenylbutyl, methylbenzyl, phenyl, tolyl, carbomethoxy, carboethoxy, carbopropoxy and carbobutoxy.

Preferably, $R^1$ and $R^2$ are ethyl, benzyl, carbomethoxy and carboethoxy and in particular hydrogen, methyl and phenyl.

$R^9$ is preferably hydrogen, $C_1$-$C_{22}$-alkyl, in particular $C_1$-$C_4$-alkyl, preferably methyl, which may be substituted by hydroxyl or carboxyl, $C_3$-$C_8$-alkenyl, in particular allyl, $C_7$-$C_{12}$-aralkyl, in particular benzyl, —$CH_2$—CN or —$(CH_2)_2$—CN; further possible meanings for $R^9$ are for example the following:

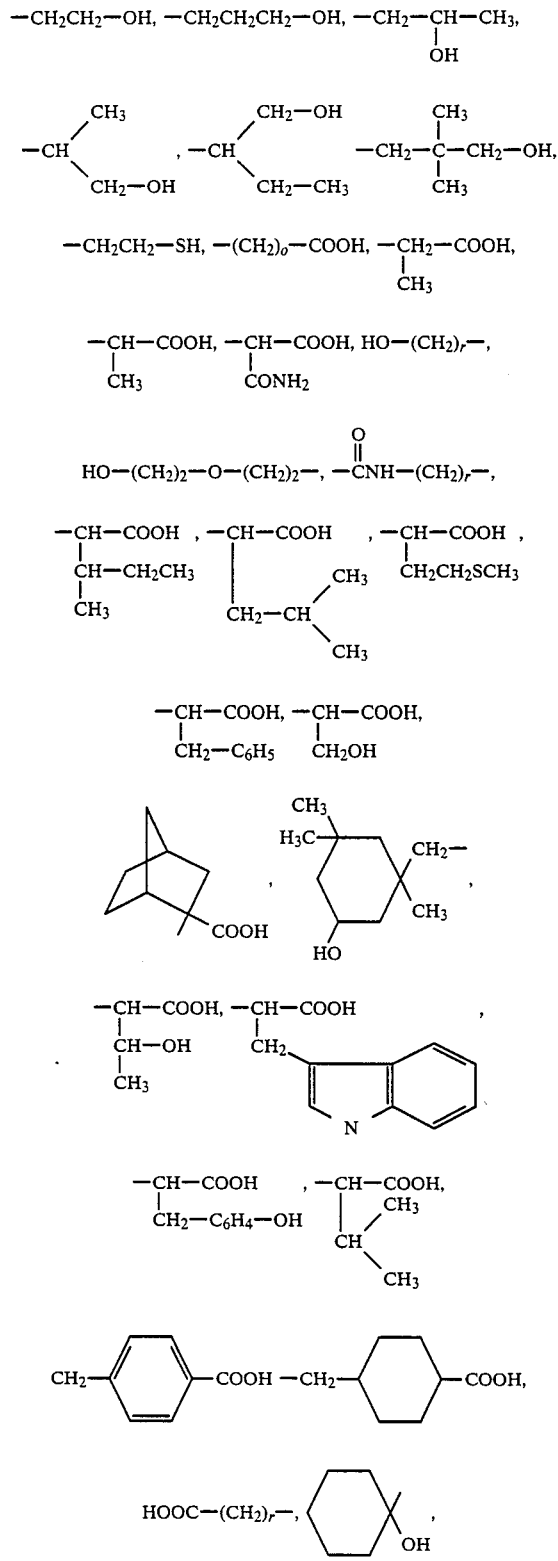

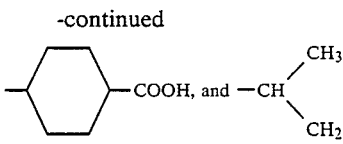

where o=1-21 and r=1-20;

n is preferably 1-40, particularly preferably 1.

The radicals $R^3$, $R^4$, $R^5$ and $R^6$ are each preferably $C_1$-$C_6$-alkyl, in particular $C_1$-$C_4$-alkyl, eg. methyl, ethyl, propyl, butyl, pentyl or hexyl. They are each particularly preferably methyl or ethyl.

For the purposes of the present invention, aryl is in particular phenyl or a $C_1$-$C_4$-alkyl or $C_1$-$C_4$-alkoxy substitution product thereof, for example tolyl or xylyl, halopheny or optionally substituted naphthyl.

$C_3$-$C_{12}$-cycloalkyl is preferably

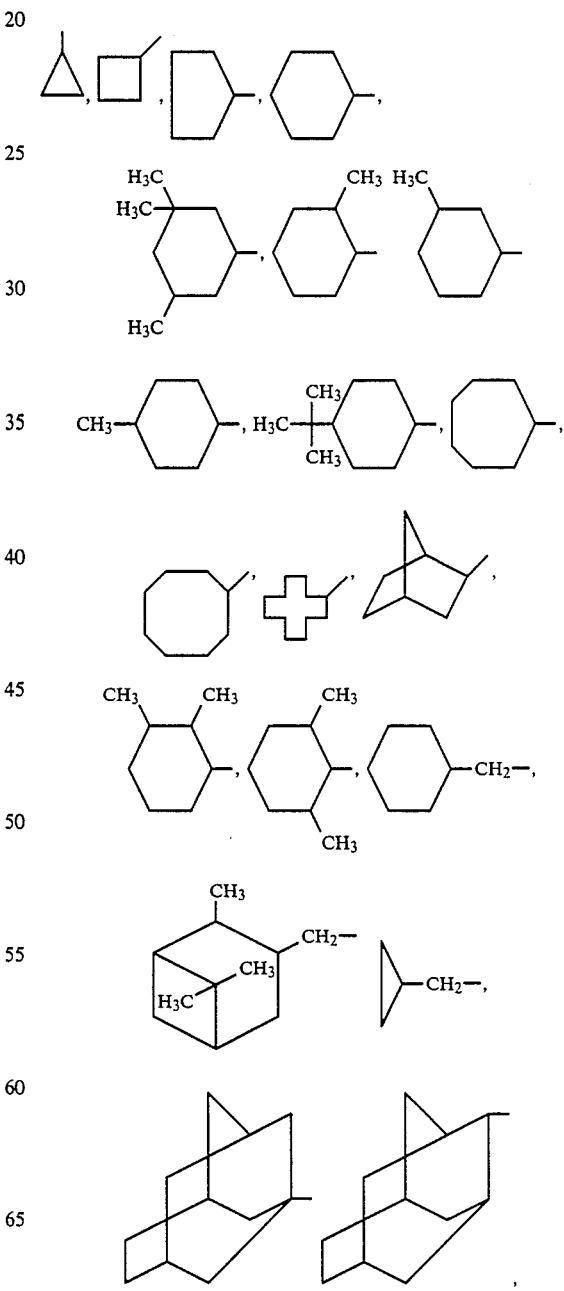

-continued

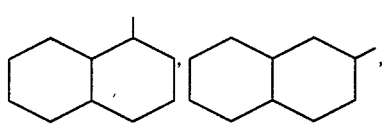

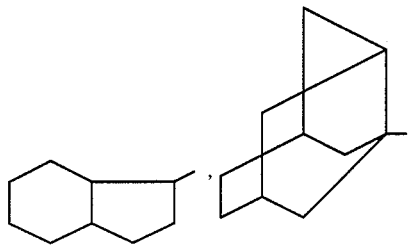

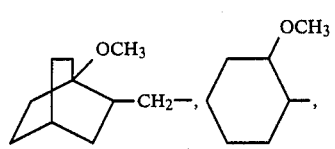

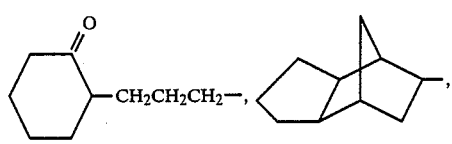

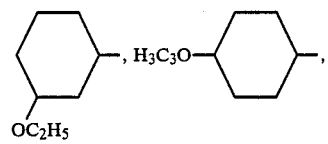

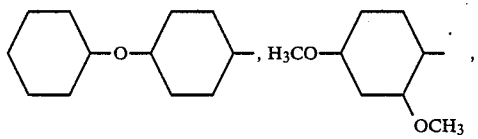

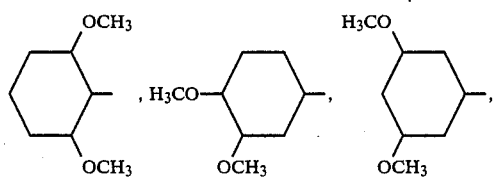

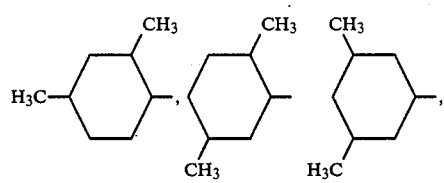

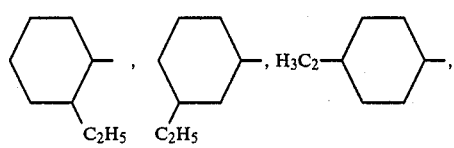

-continued

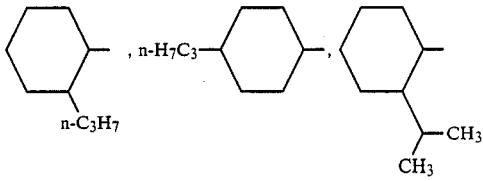

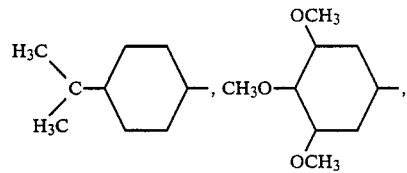

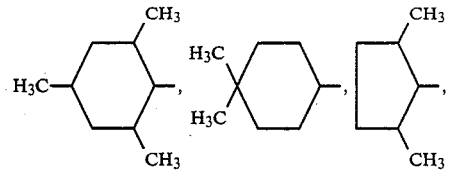

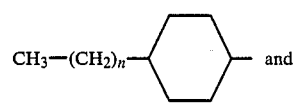 and

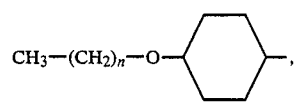

where n=1-20.

$R^7$ and $R^8$ are each preferably hydrogen or $C_1$–$C_4$-alkyl, for example methyl.

For the purposes of the present invention, ($C_1$–$C_{22}$)alkyl encompasses straight-chain and branched radicals, in particular $C_1$–$C_6$-alkyl, for example methyl, ethyl, n-propyl, i-propyl, butyl, pentyl and hexyl.

Examples of other, branched alkyl radicals are the following:

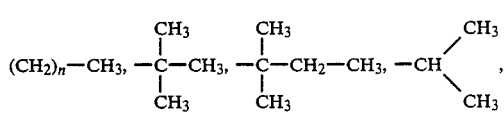

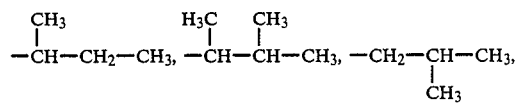

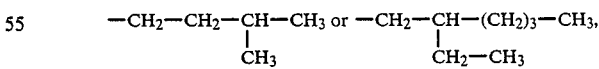

where n=0-21.

$C_7$–$C_{12}$-aralkyl emcompasses preferably $C_7$–$C_{12}$-phenylalkyl, such as benzyl or phenylethyl, and $C_1$–$C_4$-alkyl or $C_1$–$C_4$-alkoxy substitution products thereof,

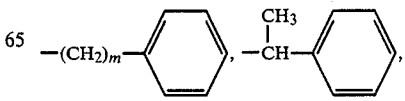

-continued

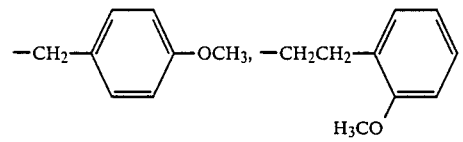

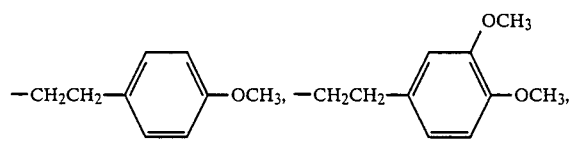

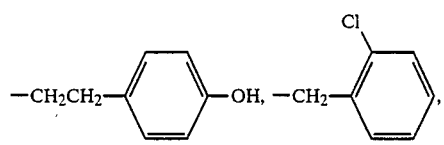

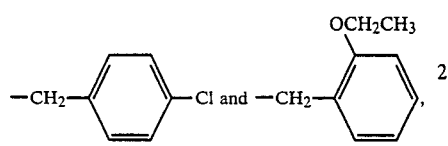

where m=1-6,

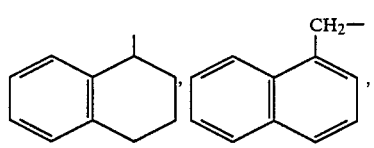

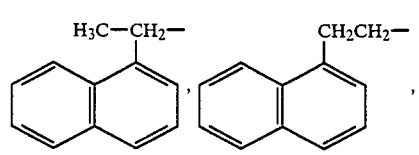

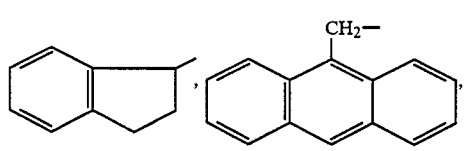

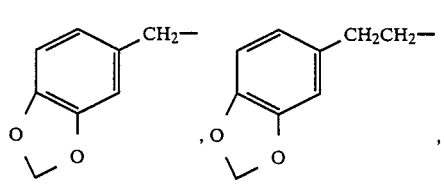

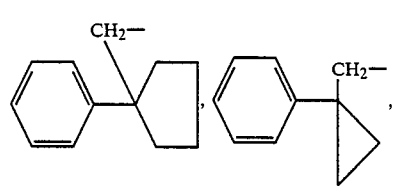

-continued

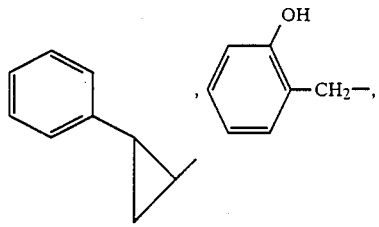

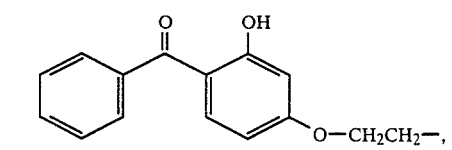

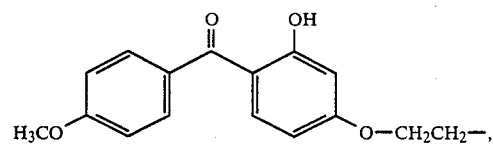

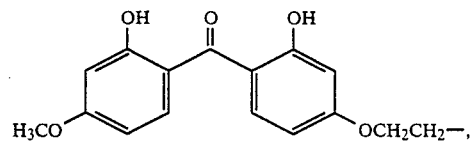

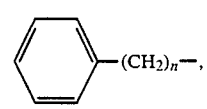

where n=1-20.

Carboxylate signifies in particular

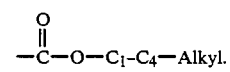

$C_3$–$C_{22}$-alkenyl emcompasses straight-chain and branched and also polyunsaturated radicals. Preference is given to $C_3$–$C_{12}$-alkenyl, for example allyl, butenyl, pentenyl, hexenyl and heptenyl.

$C_3$–$C_{22}$-alkynyl signifies straight-chain or branched monounsaturated or polyunsaturated radicals. Preference is given to $C_3$–$C_{12}$-alkynyl, for example propargyl, butynyl, pentynyl, hexynyl and octynyl.

"Oligomeric or polymeric polyamine" signifies for example the group

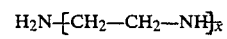

(x=1-30).

"Optionally substituted carbamoyl" signifies for example $(R^{13})_2NCO$—, where $R^{13}$ is hydrogen or $C_1$–$C_4$-alkyl.

Bridge members A and B are divalent aliphatic, araliphatic or aromatic groups which may contain, as hetero atoms, oxygen, nitrogen or sulfur. They may have, in particular in the terminal position, the groups —CO—O—, —CO—$NR^{14}$—, —$SO_2$—O— or —$SO_2$—$NR^{14}$—, where $R^{14}$ is hydrogen, $C_1$–$C_8$-alkyl, $C_7$–$C_{12}$-aralkyl, $C_2$–$C_4$-hydroxyalkyl, $C_5$–$C_7$-cycloalkyl, $C_7$–$C_{12}$-cycloalkyl-alkyl or etheroxygen-containing $C_2$–$C_9$-alkyl.

$R^{14}$ is in particular hydrogen, methyl, ethyl, propyl, butyl, pentyl, hexyl, heptyl, octyl, methylpropyl, benzyl, phenylethyl, methoxyphenylethyl, 2-hydroxyethyl, 2-hydroxypropyl, cyclopentyl, cyclohexyl, cycloheptyl or methylcyclohexyl.

Etheroxygen-containing alkyl $R^{14}$ is for example: $(CH_2)_3OCH_3$, $(CH_2)_3OC_2H_5$, $(CH_2)_3OC_3H_7$, $(CH_2)_3OC_4H_9$, $(CH_2)_2O(CH_2)_2OCH_3$, $(CH_2)_2O(CH_2)_2OC_2H_5$, $(CH_2)_2O(CH_2)_2OC_3H_7$, $(CH_2)_3O(CH_2)OC_4H_9$, $(CH_2H_4O)_3C_3(CH_2H_4O)_3C_2H_5$, $(C_2H_4O)_3C_4H_9$, $$CH_2CHOCH_3, \; CH_2CHOC_2H_5,$$
$$\quad | \qquad\qquad\quad |$$
$$\;CH_3 \qquad\qquad\; CH_3$$

$$(CH_2CHO)_2CH_3 \text{ or } CH_2CHOC_4H_9.$$
$$\quad\;\; | \qquad\qquad\qquad\quad |$$
$$\;\; CH_3 \qquad\qquad\qquad CH_3$$

A and B are in particular alkylene, cycloalkylene, aralkylene, or CO- or $SO_2$-substituted alkylene or aralkylene.

Specific bridge members are for example:

$-(CH_2)_p-$, $-(CH_2)_pCH=CH-$, $-(CH_2)_p-C\equiv C-$, $-(CH_2)_q-C_6H_4-$, $-(CH_2)_q-$cyclohexyl-H, $-(CH_2)_q-$cyclopentyl-H, $-(CH_2)_p-C_6H_4-(CH_2)_p-$, $-(CH_2)_2O-$, $-(CH_2)_2O(CH_2)_2-$, $-(CH_2)_3O(CH_2)_2-$, $-CH-CH_2-O(CH_2)_2-$, $-(CH_2)_2OCH-CH_2-$,
$\;\;|\qquad\qquad\qquad\qquad\qquad\qquad\;\;|$
$CH_3 \qquad\qquad\qquad\qquad\qquad\;\; CH_3$ $-CH-CH_2OCH-CH_2-$, $-C-(CH_2)_q-$,
$\;\;|\qquad\qquad\;\;|\qquad\qquad\quad\;\|$
$CH_3 \qquad\; CH_3 \qquad\qquad O$ $-C-(CH_2)_q-O-(CH_2)_q-C-$, $-SO_2-C_6H_4-$,
$\|\qquad\qquad\qquad\qquad\qquad\|$
$O\qquad\qquad\qquad\qquad\qquad O$ $-C-C_6H_4-$, $-C-(CH_2)_q-C_6H_4-$,
$\|\qquad\qquad\;\;\|$
$O\qquad\qquad\; O$ $-C-C_6H_4-C-$, $-C-(CH_2)_q-C-$,
$\|\qquad\qquad\|\quad\;\;\|\qquad\qquad\;\|$
$O\qquad\qquad O\quad\; O\qquad\qquad O$ $-CH_2-CH-(CH_2)_4-$, $-CH-CH_2-$, $-CH_2-CH=CH-$,
$\qquad\;|\qquad\qquad\qquad\qquad\;\;|$
$\;\;C_2H_5\qquad\qquad\qquad\; CH_3$ $-C-CH-CH_2-$, $-C-C-CH_2-$, $-CH_2-$, $-CH-$,
$\|\;\;|\qquad\qquad\;\|\;\;|\qquad\qquad\qquad\qquad\;\;|$
$O\; CH_3 \qquad\;\; O\; CH_3\qquad\qquad SH\qquad CH_3$
$\qquad\qquad\qquad\quad\;|$
$\qquad\qquad\qquad\;\; CH_3$ $-CH_2-$, $-CH-$, $\quad$ $CH_3$,
$\;\;|\qquad\;\;|\qquad\qquad\;\;|$
$CONH_2\; CH-CH_2-CH_3\;\; CH_2-CH$
$\qquad\qquad\;|\qquad\qquad\qquad\qquad\;|$
$\qquad\qquad CH_3\qquad\qquad\qquad\; CH_3$ $-CH-$, $-CH-$, $-CH-$, $-CH-$,
$\;\;|\qquad\qquad\;|\qquad\qquad\;|\qquad\quad\;\;|$
$CH_2-CH_2-SCH_3\; CH_3-C_6H_5\; CH_2OH\; CH-OH$
$\qquad\qquad\qquad\qquad\qquad\qquad\qquad\qquad\quad|$
$\qquad\qquad\qquad\qquad\qquad\qquad\qquad\quad CH_3$ $-CH-$, $-CH-$, $-CH-$,
$\;\;|\qquad\qquad\quad|\qquad\qquad\;\;|$
$CH_2-indolyl\; CH_2-C_6H_4OH\; CH(CH_3)_2$ $-C-CH-(CH_2)_4-$, $-C-CH_2-CH-CH_2-$,
$\|\;\;|\qquad\qquad\qquad\quad\|\qquad\qquad\;\;|$
$O\; C_2H_5\qquad\qquad\quad\; O\qquad\qquad CH_3$ $-C-CH_2-O-CH_2-$ and
$\|$
$O$ $-C-(CH_2)_7-CH=CH-(CH_2)_8-$,
$\|$
$O$ where p=1-20 and q=0-4.

Further example of bridge members —B— are the following:

[diketone bridge], $-N-CO-N-$ with $(CH_2)_q H$ substituents, $-C(O)-N(H)-(CH_2)_p-N(H)-C(O)-$, $-C(O)-N(H)-C_6H_4-N(H)-C(O)-$, $-C(O)-N(H)-C_6H_4-C_6H_4-N(H)-C(O)-$, $-C(O)-N(H)-C_6H_4-O-C_6H_4-N(H)-C(O)-$, $-C(O)-N(H)-C_6H_4-S-C_6H_4-N(H)-C(O)-$, $-C(O)-N(H)-C_6H_4-SO_2-C_6H_4-N(H)-C(O)-$, $-C(O)-N(H)-C_6H_4-SO-C_6H_4-N(H)-C(O)-$, -continued
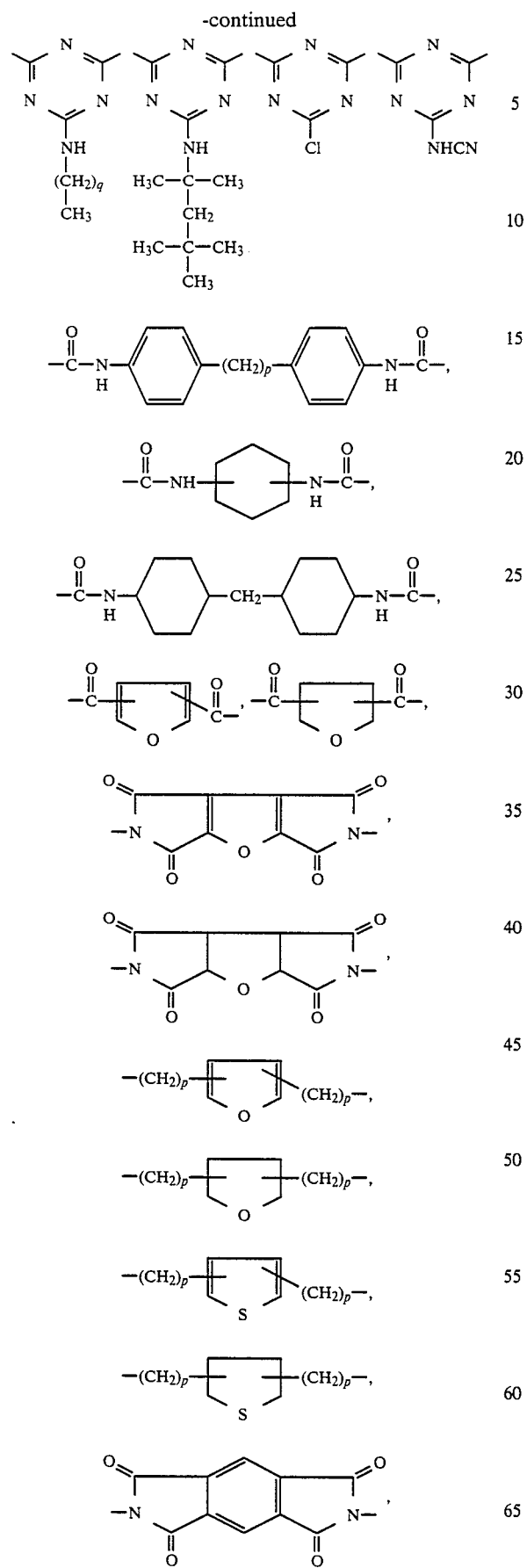
-continued
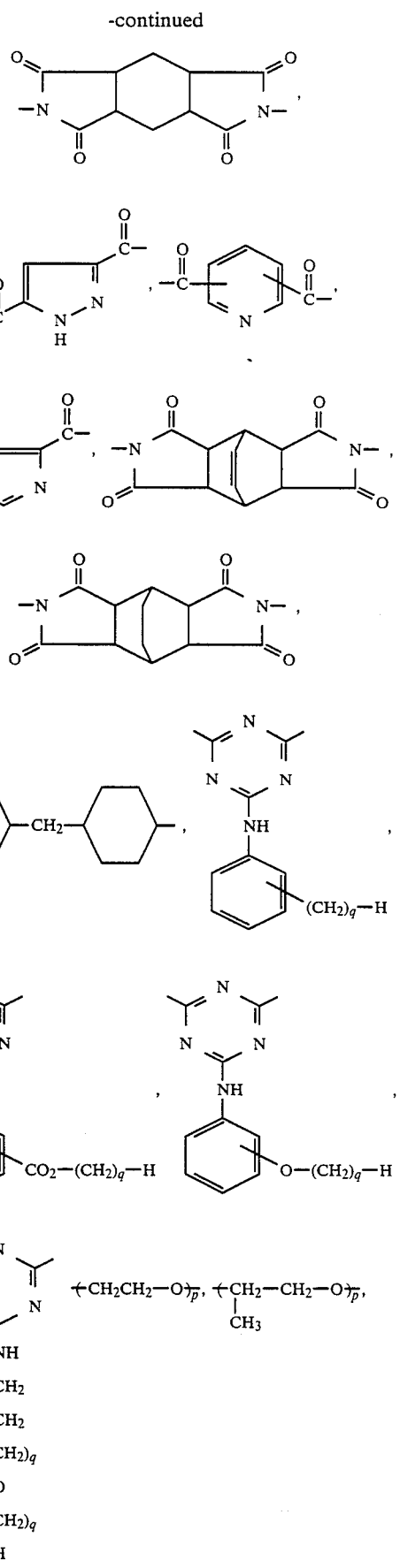

-continued

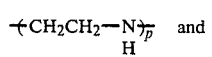 and 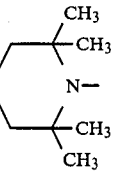

where p and q are as defined above.

Preferred bridge members are $(CH_2)_n$ where n is in particular 1–5, specifically 1, 2 or 5.

Insofar as heterocyclics, in particular nonaromatic heterocyclics, are present in the compounds according to the invention, these heterocyclics can comprise for example the following:

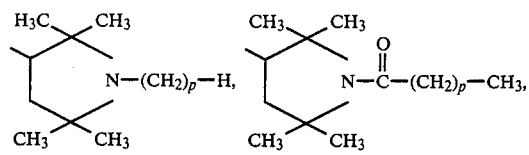

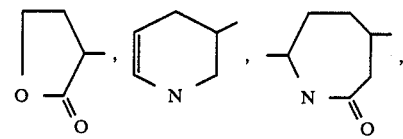

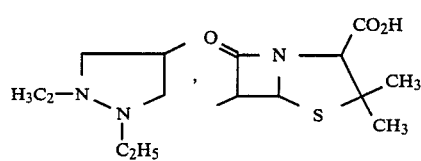

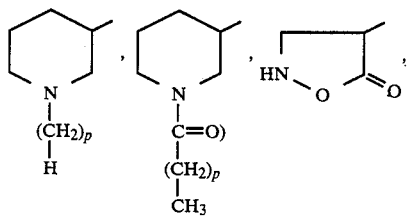

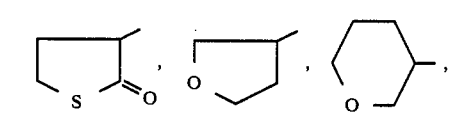

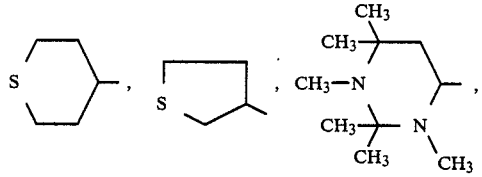

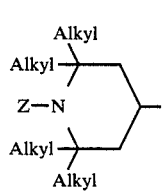

where Z = hydrogen, alkyl C-acyl or HO—
and p = 1–20.

Examples of urea groups are the following:

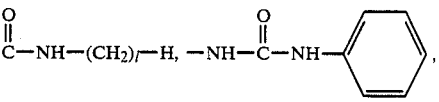

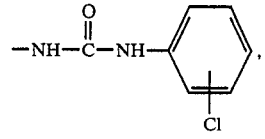

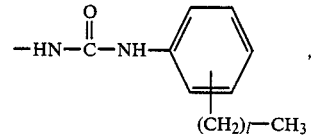

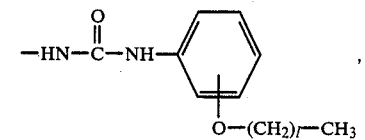

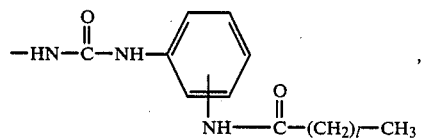

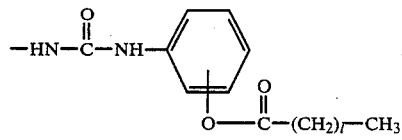

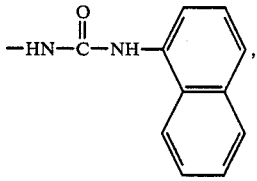

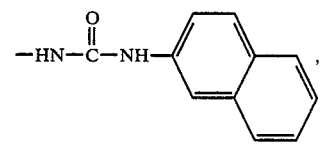

where l = 0–22.

Examples of urethane groups are the following:

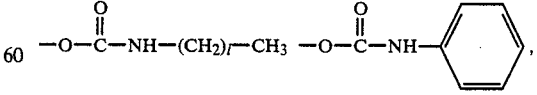

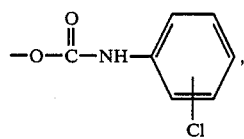

-continued

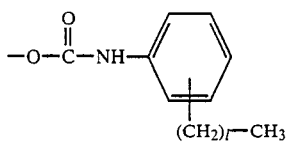

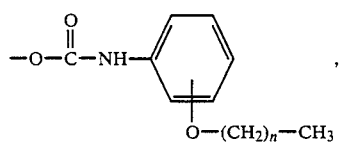

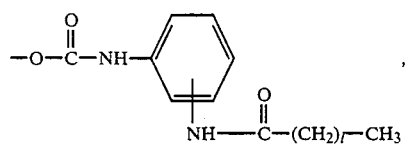

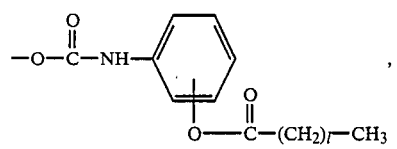

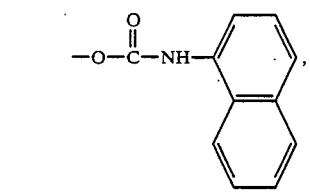

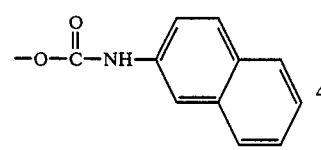

where l=0-22.

Y and Z are independently of each other in particular oxygen but also sulfur or —NR$^{10}$.

R$^{10}$ is hydrogen, C$_1$-C$_8$-alkyl or C$_7$-C$_{12}$-aralkyl.

R$^{11}$ and R$^{12}$ are independent of each other in particular hydrogen, but also

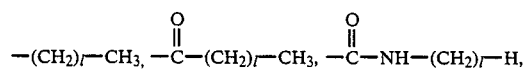

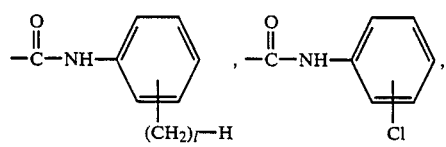

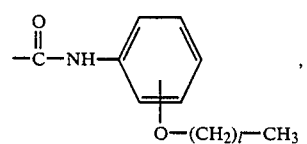

-continued

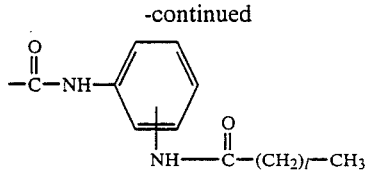

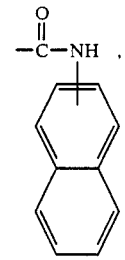

where l=0-22.

If R$^{11}$ and R$^{12}$ form a ring system together with the nitrogen atom to which they are bonded, this ring system can be for example:

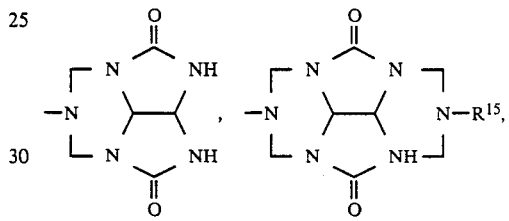

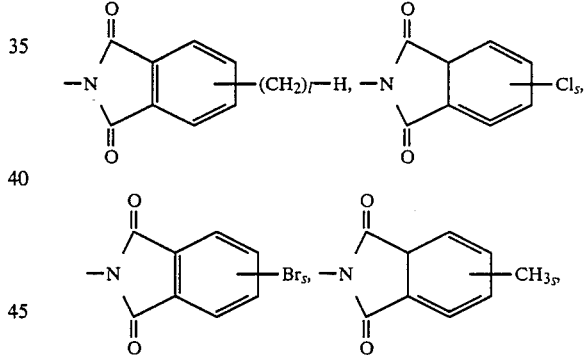

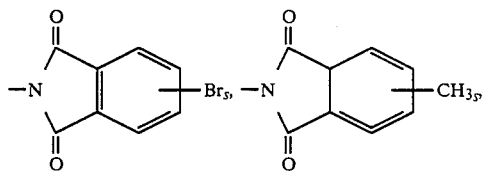

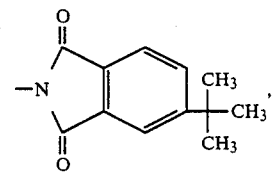

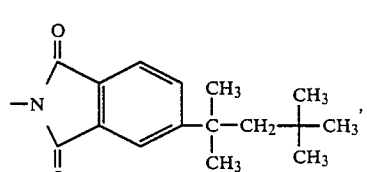

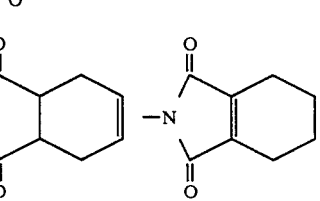

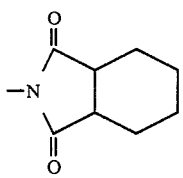

where l=0-22 and s=1-4,
and $R^{15}$ can take on all the aforementioned meanings of $R^9$.

Compounds of the general formula (I) where n=1 and where the bridge member A has —CO—O—, —CO—NR$^9$—, —SO$_2$—O— or —SO$_2$—NR$^9$— groups can be prepared by reaction of compounds of the general formula II

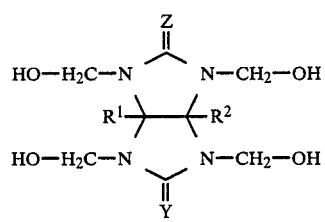

analogously to the process of FR-A-2,291,203 with aminocarboxylates H$_2$N—B—COOR or aminosulfonic acids H$_2$—B—SO$_3$ or the corresponding alkyl esters, for example ethyl, and subsequent catalyzed transesterification or esterification with substituted piperidine-4-amines or piperidin-4-ols. The following scheme shows the sequence of reactions for an exemplary compound III.

acid or preferably a tetraalkyl orthotitanate, such as tetrabutyl orthotitanate.

Compounds of the general formula I can further be prepared by reaction of compounds of the general formula II with compounds of the general formula IV

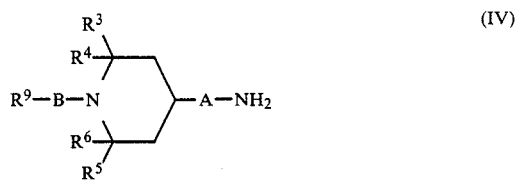

These compounds of the formula II can be prepared in situ by reaction of compounds of the general formula V

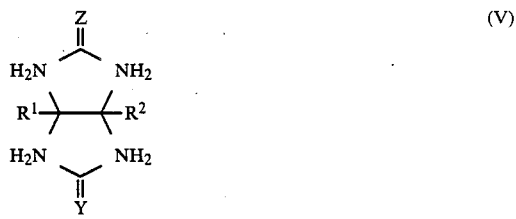

with formaldehyde or a source thereof.

The compounds of the formula I where B—R$^9$=H can be converted by literature methods, for example by reductive amination, into compounds where for example B—R$^9$=CH$_3$.

Compounds of the general formula I where R$^9$ is —(CH$_2$)—CN can also be prepared in an advantageous manner by reaction of compounds of the general formula VI

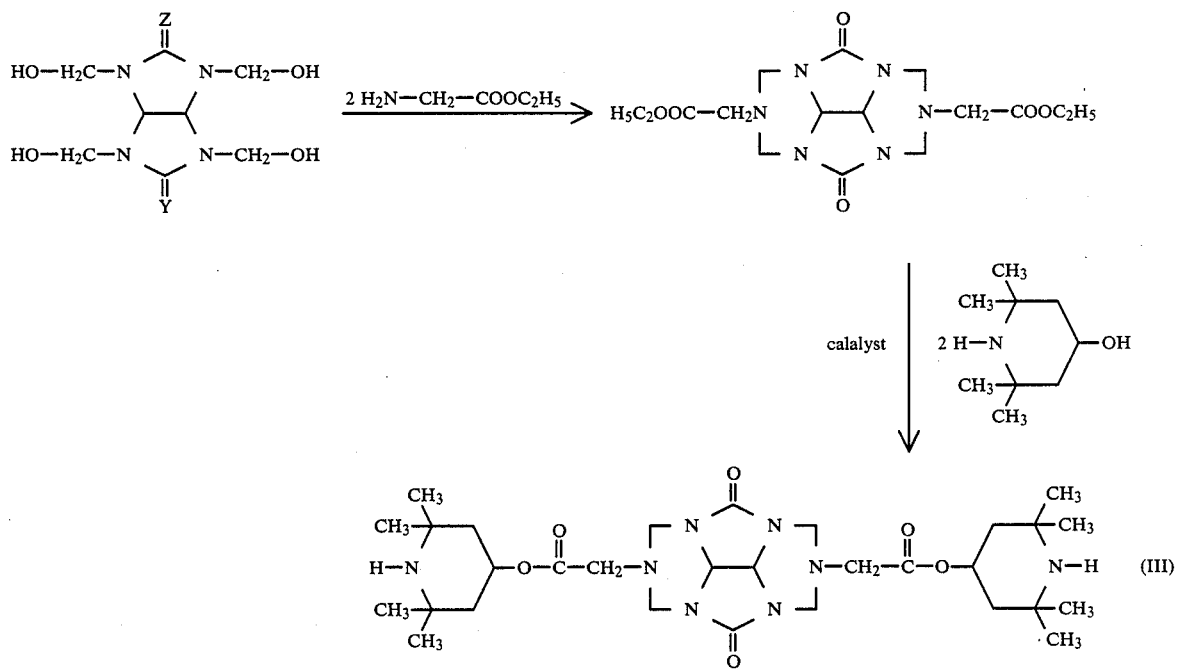

The catalyst of the second reaction step can be an alkali metal alcoholate, such as sodium methylate, an alkali metal hydroxide, such as sodium hydroxide, an

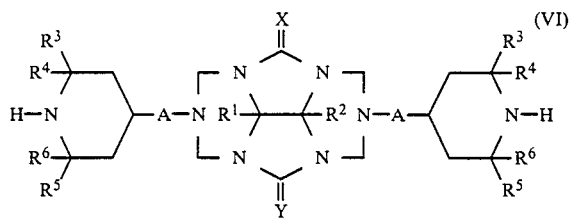

(VI)

with glycollonitrile or a source thereof. The reaction of glycollonitrile with sterically hindered amines is described in DE-A-3,208,570.

The compounds according to the invention can be present in the form of the free bases as hydrates or as salts. Suitable anions come for example from inorganic acids and in particular organic carboxylic acids and also organic sulfonic acids.

Inorganic anions are for example chloride, bromide, sulfate, isosulfate, tetrafluoroborate, phosphate and thiocyanate.

Carboxylic acid anions are for example formate, acetate, propionate, hexanoate, cyclohexanoate, lactate, stearate, dodecylbenzoate, benzoate, acrylate, methacrylate, citrate, malonate, succinate and anions of polycarboxylic acids having up to 3,000 COOH groups.

Sulfonic acid anions are for example benzenesulfonate and tosylate.

The compounds according to the invention have remarkably good stabilizing properties, have no self-color, are highly compatible with organic polymers and have a low vapor pressure.

The compounds according to the invention are suitable for stabilizing organic materials, especially plastics, to degradation by light and heat and to damage by metals or metal ions, which can be present in traces in the organic material. They are added to the plastics to be stabilized in a concentration of from 0.01 to 5% by weight, preferably from 0.02 to 1% by weight, before, during or after polymer formation.

The compounds according to the invention can be mixed with the plastics to be stabilized by any known apparatus and method for mixing stabilizers or other additives in the polymers.

The plastics stabilized by one of the compounds according to the invention may also contain further additives, for example antioxidants, light stabilizers, metal deactivators, antistats, flame retardents, pigments and fillers.

Examples of antioxidants and light stabilizers which can be added to the plastics besides the compounds according to the invention are compounds based on sterically hindered phenols or sulfur- or phosphorus-containing costabilizers.

Specific examples of such phenolic antioxidants are 2,6-di-tert.-butyl-4-methylphenol, n-octadecyl-β-(3,5-di-tert.-butyl-4-hydroxyphenyl)propionate, 1,1,3-tris(2-methyl-4-hydroxy-5-tert.-butylphenyl)butane, 1,3,5-trimethyl-2,4,6-tris(3,5-di-tert.-butyl-4-hydroxybenzyl)-benzene, 1,3,5-tris(3,5-di-tert.-butyl-4-hydroxybenzyl) isocyanurate, 1,3,5-tris[β-(3, 5-di-tert.-butyl-4-hydroxyphenyl)propionyloxyethyl]isocyanurate, 1,3,5tris(2, 6-dimethyl-3-hydroxy-4-tert.-butylbenzyl) isocyanurate, pentaerythritol tetrakis[β-(3,5-di-tert.-butyl-4-hydroxyphenyl)propionate].

Examples of phosphorus-containing antioxidants are tris(nonylphenyl) phosphite, distearyl pentaerythritol diphosphite, tris(2,4-di-tert.-butylphenyl) phosphite, tris(2-tert.-butyl-4-methylphenyl) phosphite, bis(2,4-ditert.-butylphenyl) pentaerythritol diphosphite and tetrakis(2,4-di-tert.-butylphenyl)-4,4'-biphenylene diphosphite.

Examples of sulfur-containing antioxidants are dilauryl thiodipropionate, dimyristyl thiodipropionate, distearyl thiodipropionate, pentaerythritol tetrak is (β-laurylthiopropionate) and pentaerythritol tetrak is (β-hexylthiopropionate).

Further antioxidants and light stabilizers which may be used together with the compounds according to the invention are for example 2-(2'-hydroxyphenyl)benzotriazoles, 2-hydroxybenzophenones, aryl esters of hydroxybenzoic acid, α-cyanocinnamic acid derivatives, nickel compounds and oxalic dianilides.

Examples of organic polymers which can be stabilized by the compounds according to the invention are:

polymers of mono- and diolefins, eg. low or high density polyethylene, linear low density polyethylene, polypropylene, polyisobutylene, polybutene-1, polyisoprene, polybutadiene and also copolymers of mono- or diolefins or mixtures thereof;

copolymers of mono- or diolefins with other vinyl monomers, eg. ethylene/alkyl acrylate copolymers, ethylene/alkyl methacrylate copolymers, ethylene/vinyl acetate copolymers or ethylene/acrylic acid copolymers;

polystyrene;

copolymers of styrene or α-methylstyrene with dienes or acrylic derivatives, eg. styrene/butadiene, styrene/acrylonitrile, styrene/ethyl methacrylate, styrene/butadiene/ethyl acrylate, styrene/acrylonitrile/methacrylate;

ABS, MBS or similar polymers;

halogen-containing polymers, eg. polyvinyl chloride, polyvinyl fluoride, polyvinylidene fluoride and copolymers thereof;

polymers derived from α,β-unsaturated acids and derivatives thereof, such as polyacrylates, polymethacrylates, polyacrylamides and polyacrylonitriles;

polymers derived from unsaturated alcohols and amines or their acrylic derivatives or acetals, such as polyvinyl alcohol and polyvinyl acetate;

polyurethanes, polyamides, polyureas, polyesters, polycarbonates, polysulfones, polyether sulfones and polyether ketones.

Further organic polymers which can be stabilized with the compounds according to the invention are industrial coatings. Of these, baking finish coatings, in particular automotive coatings, preferably of the two-build variety, are particularly noteworthy.

Here too the abovementioned antioxidants and light stabilizers may be used in addition.

The compounds according to the invention can, if solid, be added to the coating solution in a solid or dissolved form or, if liquid, can be added as such. In this connection, their excellent solubility in coating systems is of particular advantage.

Preference is given to using the compounds according to the invention in paints, polyamides or polyolefins, preferably ethylene and propylene polymers. The invention is illustrated in detail by the Examples below.

EXAMPLE 1

(a) 349 g (=2.50 mol) of glycine ethyl ester hydrochloride were dissolved in 380 ml of water. 100 g of solid sodium hydroxide were added a little at a time with ice-cooling. This was followed by 656 g (=1.25 mol) of a 50% strength aqueous solution of tetramethylolacetylenediurea. The mixture was refluxed for 2 h, cooled down and filtered with suction, the filter residue was washed with a little water and dried at 80° C. in a water jet vacuum to leave 199 g (40%) of a colorless solid having a melting point of 164° C.

(b) 13.6 g of tetracyclo[5.5.2.0$^{5,13}$.0$^{11,14}$]-1,3,5,7,9,11-hexaaza-3,9-bis[carbethoxymethyl]-6,12-dioxotetradecane from (a), 10.9 g of 4-hydroxy-2,2,6,6-tetramethylpiperidine and 1.5 ml of tetrabutyl orthotitanate were refluxed in 50 ml of xylene under nitrogen for 10 h. After cooling down, the precipitate obtained was filtered off with suction, washed with xylene, dried and treated with hot water to give 13.0 g of monohydrate as colorless crystals having a melting point of 183° C.

Calculated: C 56.8; H 7.9; N 17.6; O 17.6; found: C 56.4; H 8.2; N 17.6; O 17.9

EXAMPLE 2

41.4 g of the product of Example 1a, 35.7 g of 4-hydroxy-1,2,2,6,6-pentamethylpiperidine and 4.5 ml of tetrabutyl orthotitanate were refluxed in 150 ml of xylene under nitrogen for 12.5 h. The precipitate obtained was filtered off with suction at room temperature, washed with xylene and recrystallized from isopropanol to give 18.6 g of monohydrate as colorless crystals having a melting point of 204° C.

Calculated: C 58.0; H 8.5; N 16.9; O 16.9; found: C 58.1; H 8.3; N 17.3; O 16.0

EXAMPLE 3

59.1 g of the product of Example 1a, 46.8 g of 4-amino-2,2,6,6-tetramethylpiperidine and 6 ml of tetrabutyl orthotitanate were refluxed in 225 ml of xylene for 8 h. Working up as in Example 2 produced 23.3 g of tetrahydrate as colorless crystals having a melting point of 201° C. By concentrating the solvent to 250 ml it was possible to isolate a further 18.6 g having a melting point of 199° C.

Calculated: C 52.3; H 8.8; N 20.3; O 18.6; found: C 52.0; H 8.6; N 20.3; O 19.5

EXAMPLE 4

41 g (0.083 mol) of tetracyclo-[5.5.2.0$^{5,13}$.0$^{11,14}$]-1,3,5,7,9,11-hexaaza-6,12-dioxo-3,9-di(2,2,6,6-tetramethyl-4-piperidinyl)-tetradecane and 20.3 g (0.25 mol) of a 70% strength aqueous solution of hydroxyacetonitrile were boiled in 125 ml of ethanol for 15 h. This is followed by cooling down, filtering off with suction, washing with ethanol until the runoff was colorless, and drying in a waterjet vacuum at 60° C. to give 38 g (79%) of colorless crystals having a melting point of 283° C.

Calculated: C 62.1; H 8.3; N 24.1; O 5.6; found: C 62.1; H 8.5; N 24.1; O 5.6

30 g (1.0 mol) of paraformaldehyde, 85 g (1.0 mol) of acetonecyanohydrin and 2.4 g of potassium carbonate were stirred at room temperature in 24 ml of ethanol saturated with potassium carbonate for 2 hours. Phosphoric acid was added to adjust to pH 6, followed by 24 ml of 0.5% strength phosphoric acid and 350 ml of ethanol. 125.5 g (0.25 mol) of tetracyclo-[5.5.2.0$^{5,13}$.0$^{11,14}$]-1,3,5,7,9,11-hexaaza-6,12-dioxo-3,9-di(2,2,6,6-tetramethyl-4-piperidinyl)-tetradecane were then added, and the mixture was then heated under reflux for 5 hours. The product was worked up as in Example 4 to give 123 g (85% of theory) of the product of Example 4.

EXAMPLES 6 to 9

The method of Example 5 was used to prepare the compounds

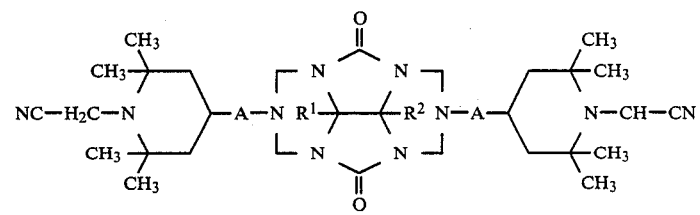

having the radicals and melting points specified in the Table below.

TABLE

| Example | R$^1$ | R$^2$ | | Melting point [°C.] |
|---|---|---|---|---|
| 6 | CH$_3$ | H | — | 288 |
| 7 | C$_6$H$_5$ | C$_6$H$_5$ | — | 308–309 |
| 8 | H | H | —CH$_2$CO— (O double bond) | 202–203 |
| 9 | H | H | —CH$_2$CNH— (O double bond) | 280 |

EXAMPLE 10

40 g of the product of Example 4 and 5 g of Raney nickel were suspended in 500 ml of toluene in a 1-l lift autoclave. 40 g of ammonia were condensed in, hydrogen was introduced to establish a pressure of 100 bar, and the temperature was raised to 80° C. Hydrogenation was carried out under a pressure of 300 bar until no further hydrogen absorption was observed.

Two such batches were combined and filtered, and the filtrate was concentrated. The residue was recrystallized from toluene, dried at 80° C. and boiled up with water to remove water-soluble impurities.

Yield: 39.6 g of the hydrate of the compound of the formula

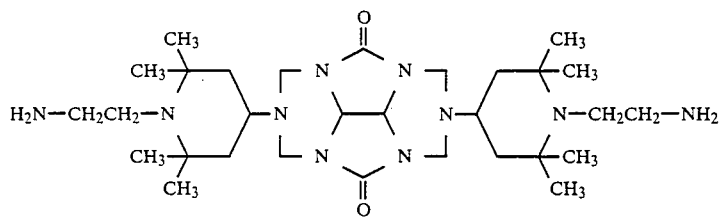

having a melting point of 203–204° C.

EXAMPLE 11

To 7.7 g of the product of Example 10 in 75 ml of pyridine were added dropwise 2.4 g of adipoyl chloride. The mixture was maintained at 50–60° C. for 3.5 h, cooled down and poured onto 150 ml of petroleum ether. The residue was filtered off with suction, stirred with 10% strength sodium hydroxide solution for 10 minutes, filtered off with suction and washed with water. Drying was followed by hot solution in a little isobutanol, filtration, stirring of the filtrate into petroleum ether and removal of the resulting precipitate by filtration with suction. Yield: 2.6 g of oligomers of the formula

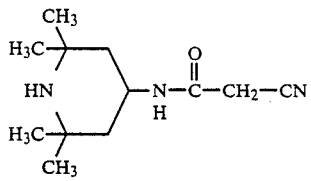

having a melting point of 150–152° C. were filtered off with suction.

(b) 44 g of the product of (a) were hydrogenated in 400 ml of methanol under 200 bar in the presence of 10 g of Raney nickel and 40 g of ammonia to a constant pressure. The reaction mixture was filtered, and the

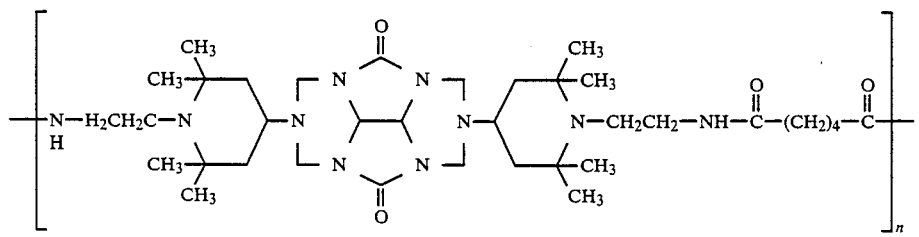

filtrate was concentrated and subjected to a vacuum distillation, which led to the isolation of 21.5 g of the compound of the formula

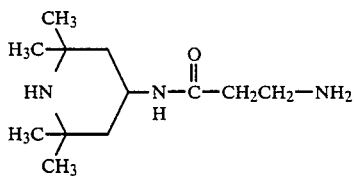

having a boiling point of 165–169° C. at 0.5 mmHg. On prolonged standing, the oil obtained formed crystals having a melting point of 74–76° C.

(c) 11.3 g of the product of (b) and 13.1 g of a 50% strength aqueous solution of tetramethylolacetylenediurea were boiled in 300 ml of isobutanol under a water separator until no further water was separated off. The solution was concentrated, and the residue was recrystallized from acetonitrile. Yield: 7.1 g of the hydrate of the compound of the formula having a melting point of 274° C. The average molecular weight was 2570 g/mol (by vapor pressure osmometry in chloroform).

EXAMPLE 12

(a) 169.5 g of ethyl cyanoacetate and 232.5 g of 2,2,6,6-tetramethyl-4-aminopiperidine were boiled in 200 ml of ethanol for 8 h. After cooling down 5 g of active carbon and 450 ml of ethyl acetate were added, and the mixture was heated up and filtered hot. After cooling down, 169.2 g of the compound of the formula

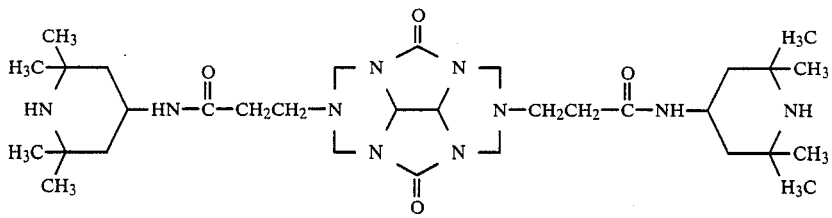

having a melting point of 125–127° C.

We claim:

1. A compound of the formula (I)

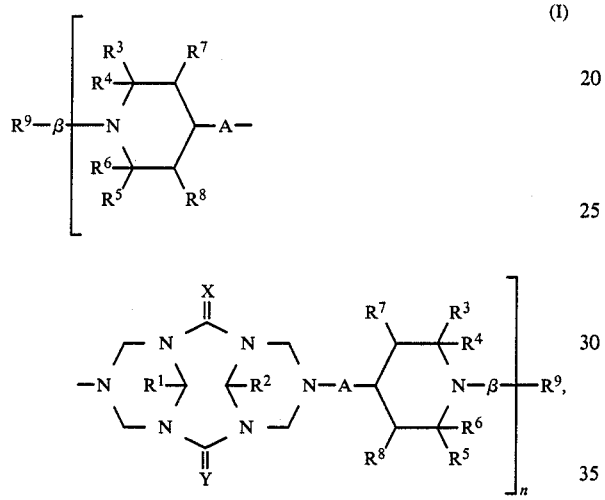

where n is a number from 1 to 70, $R^1$ and $R^2$ are independently of each other hydrogen, $C_1$–$C_6$-alkyl, $C_7$–$C_{12}$-phenylalkyl which may be substituted by $C_1$–$C_4$-alkyl, $C_1$–$C_4$-alkoxy or chlorine, phenyl, toloyl, carbo-$C_1$–$C_4$-alkoxy, or $R^1$ and $R^2$ together form a tetra-, penta- or hexamethylene group or a radical of the formula

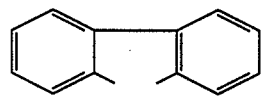

$R^3$, $R^4$, $R^5$ and $R^6$ are independently of each other $C_1$–$C_6$-alkyl, $R^7$ and $R^8$ are indpendently of each other hydrogen or $C_1$–$C_4$-alkyl or together with the associated carbon atom form a

group,

X and Y independently of each other have the meanings oxygen or sulfur, $R^9$ is hydrogen, $C_1$–$C_{22}$-alkyl which may be substituted by hydroxyl or carbo-$C_1$–$C_4$-alkoxy, $C_3$–$C_{22}$-alkenyl, $C_3$–$C_{22}$-alkynyl, $C_7$–$C_{12}$-phenylalkyl which may be substituted by $C_1$–$C_4$-alkyl, $C_1$–$C_4$-alkoxy or chlorine or —$(CH_2)_k D$ where k is a number from 1 to 10 and D is —CN, —$NH_2$, —$NHR^{11}$ or —$NR^{11}R^{12}$, where $R^{11}$ and $R^{12}$ are identical or different and each is $C_1$–$C_{22}$-alkyl, $C_1$–$C_{23}$-alkyl-carbonyl,

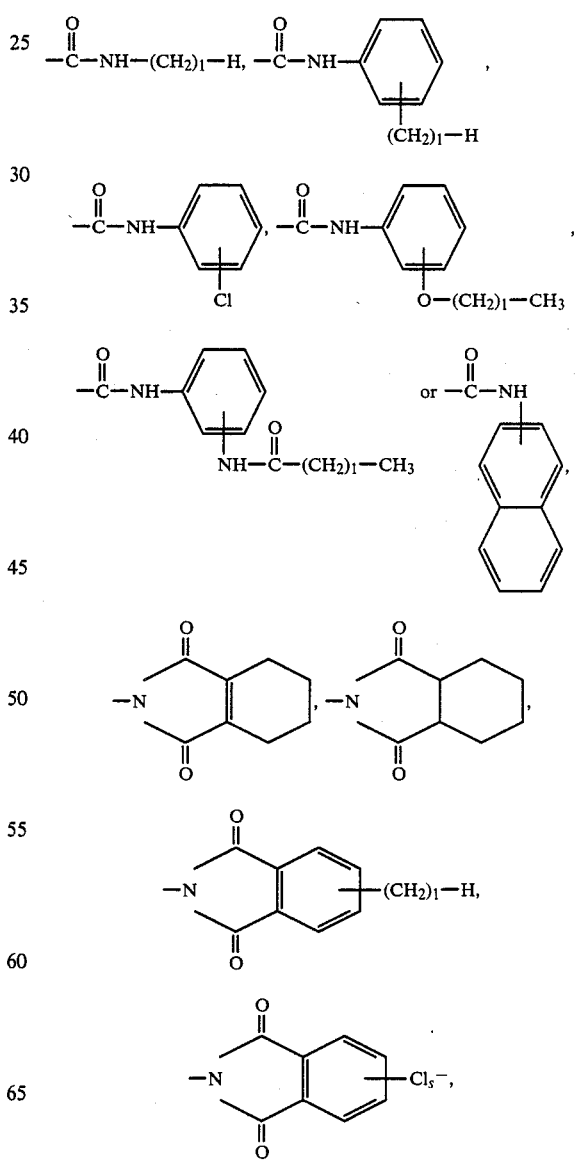

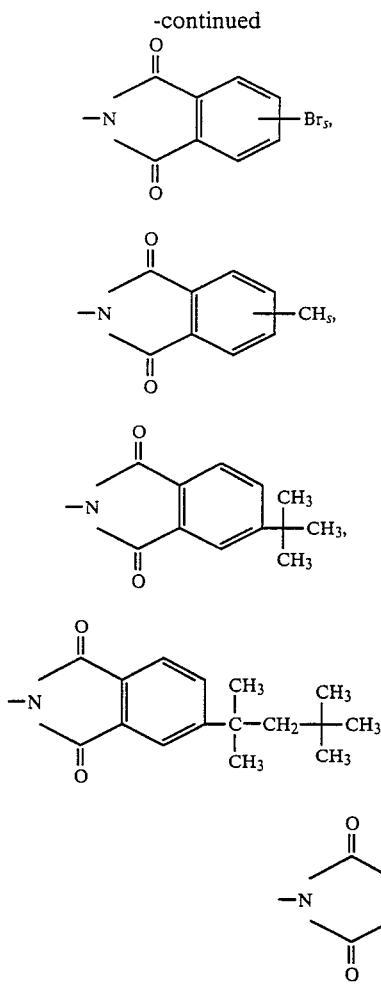

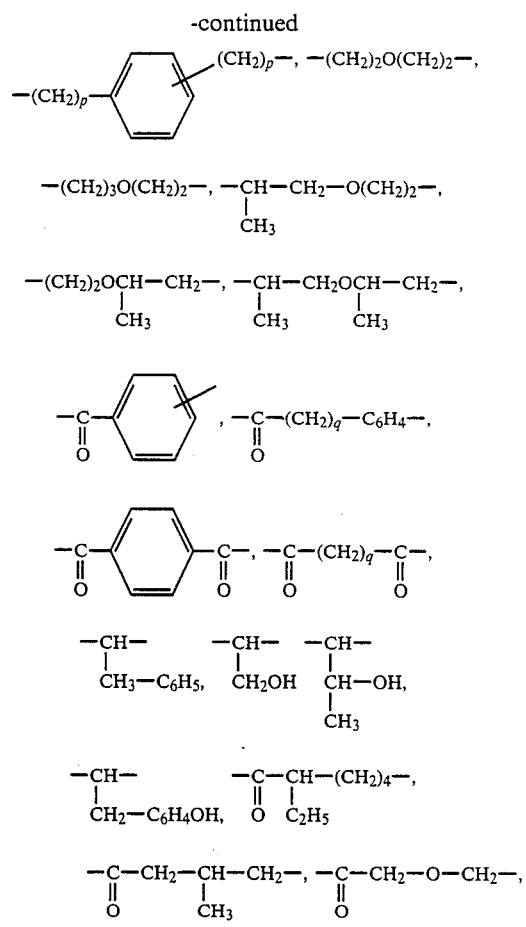

where l is 0–22 and s is 1–4, $C_2$–$C_{22}$-alkenyl, $C_3$–$C_{22}$-alkynyl, $C_3$–$C_{12}$-cycloalkyl, $C_7$–$C_{12}$-phenylalkyl which may be substituted by $C_1$–$C_4$-alkyl, $C_1$–$C_4$-alkoxy or chlorine, or oligomeric or polymeric polyamine of the formula $H_2N\text{-}[CH_2\text{-}CH_2NH]_x$ $x = 1\text{-}30$ A's are identical or different and each is a chemical bond, $C_1$–$C_{20}$-alkylene or a CO- or $SO_2$-substituted $C_1$–$C_{20}$-alkylene, with the proviso that one or more of the radicals A is a bridge member if $R^9$ does not have the meaning —$(CH_2)_k$—D, and B is a chemical bond, a bridge member of the formula

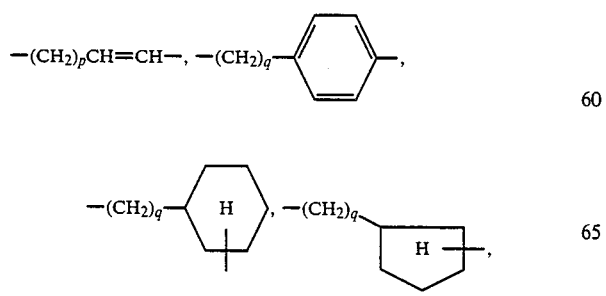

where p is 1–20 and where p is 1–20 and q=0–4,

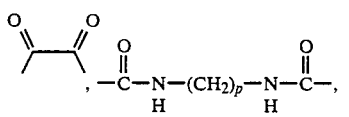

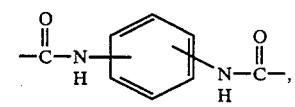

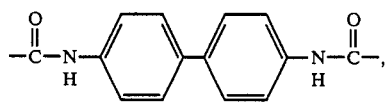

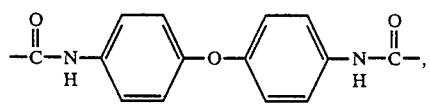

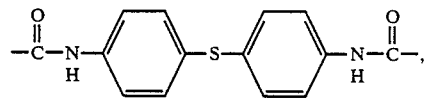

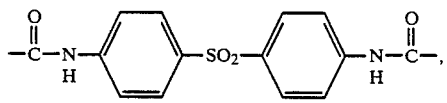

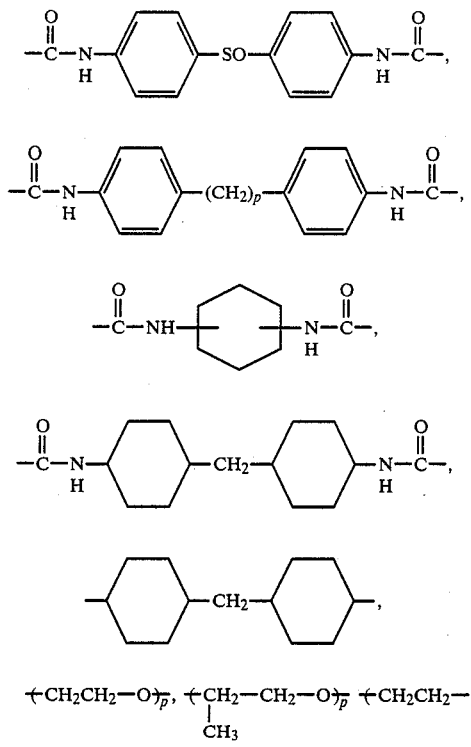

$C_1$-$C_{20}$-alkylene or CO- or $SO_2$-substituted $C_1$-$C_{20}$-alkylene, and the acid addition salts and hydrates thereof.

2. A compound as claimed in claim 1, where $R^1$ and $R^2$ are independently of each other hydrogen, methyl, ethyl, benzyl, phenyl, carbomethoxy or carboethoxy.

3. A compound as claimed in claim 1, where $R^1$ and $R^2$ are independently of each other hydrogen, methyl or phenyl.

4. A compound as claimed in claim 2, wherein X and Y are each oxygen.

5. A compound as claimed in claim 3, wherein X and Y are each oxygen.

6. A compound as claimed in claim 4, where $R^9$ is hydrogen and n is 1 or $R^9$ is —$CH_2$—CN.

7. A compound as claimed in claim 5, wherein $R^9$ is hydrogen and n is 1 or $R^9$ is —$CH_2$—CN.

8. A compound as claimed in claim 4, where $R^3$, $R^4$, $R^5$ and $R^6$ are each methyl.

9. A compound as claimed in claim 5, where $R^3$, $R^4$, $R^5$ and $R^6$ are each methyl.

10. A compound as claimed in claim 6, where $R^3$, $R^4$, $R^5$ and $R^6$ are each methyl.

11. A compound as claimed in claim 7, where $R^3$, $R^4$, $R^5$ and $R^6$ are each methyl.

12. A compound as claimed in claim 8, where A and B are each $C_1$-$C_5$-alkylene.

13. A compound as claimed in claim 9, where A and B are each $C_1$-$C_5$-alkylene.

14. A compound as claimed in claim 10, where A and B are each $C_1$-$C_5$-alkylene.

15. A compound as claimed in claim 11, where A and B are each $C_1$-$C_5$-alkylene.

16. A compound as claimed in claim 8, where A and B are each a bridge member having a —CO—O— or —CO—NH—function.

17. A compound as claimed in claim 9, wherein A and B are each a bridge member having a —CO—O— or —CO—NH—function.

18. A compound as claimed in claim 10, wherein A and B are each a bridge member having a —CO—O— or —CO—NH—function.

19. A compound as claimed in claim 11, where A and B are each a bridge member having a —CO—O— or —CO—NH—function.

* * * * *